(12) United States Patent
Rodgers et al.

(10) Patent No.: US 9,272,013 B2
(45) Date of Patent: Mar. 1, 2016

(54) METHODS FOR TREATING COMBINED RADIATION AND THERMAL INJURY

(75) Inventors: Kathleen E. Rodgers, Long Beach, CA (US); Gere S. diZerega, San Luis Obispo, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/637,038

(22) PCT Filed: Mar. 28, 2011

(86) PCT No.: PCT/US2011/030142
§ 371 (c)(1),
(2), (4) Date: Jan. 23, 2013

(87) PCT Pub. No.: WO2011/120032
PCT Pub. Date: Sep. 29, 2011

(65) Prior Publication Data
US 2013/0123190 A1 May 16, 2013

Related U.S. Application Data

(60) Provisional application No. 61/317,897, filed on Mar. 26, 2010.

(51) Int. Cl.
*A61K 38/08* (2006.01)

(52) U.S. Cl.
CPC .............. *A61K 38/08* (2013.01); *A61K 38/085* (2013.01)

(58) Field of Classification Search
None
See application file for complete search history.

(56) References Cited

U.S. PATENT DOCUMENTS

| 6,165,978 | A  | * | 12/2000 | Rodgers et al. | ............... | 514/9.4 |
| 6,455,500 | B1 |   | 9/2002  | Rodgers et al. |   |   |
| 2003/0017970 | A1 |   | 1/2003 | Rodgers et al. |   |   |
| 2003/0130196 | A1 | * | 7/2003 | Rodgers et al. | ................ | 514/14 |
| 2007/0293458 | A1 | * | 12/2007 | Shamsuddin et al. | ........ | 514/102 |

FOREIGN PATENT DOCUMENTS

| CN | 101578042 | 11/2009 |
| JP | 2002-506042 | 2/2002 |
| WO | 98/26795 | 6/1998 |
| WO | 98/33813 | 8/1998 |
| WO | WO 9833813 A2 * | 8/1998 |
| WO | 99/31125 | 6/1999 |
| WO | 99/45945 | 9/1999 |
| WO | 00/56345 | 9/2000 |

OTHER PUBLICATIONS

Rodgers et al. Accelerated recovery from irradiation injury by angiotensin peptides. Cancer Chemotherapy and Pharmacology. 2002, vol. 49, pp. 403-411.*

(Continued)

*Primary Examiner* — Jeffrey E Russel
(74) *Attorney, Agent, or Firm* — McDonnell Boehnen Hulbert & Berghoff LLP

(57) ABSTRACT

The present invention provides methods for treating a subject that has suffered combined exposure to total body ionizing irradiation and burns by administering a peptide of at least 5 amino acids of a peptide of SEQ ID NO:1 (Asp-Arg-Nle-Tyr-Ile-His-Pro), or a pharmaceutical salt thereof in an amount effective to treat the radiation effects and/or the burn.

11 Claims, 10 Drawing Sheets

(56) References Cited

OTHER PUBLICATIONS

Rodgers, et al. (2005) "Fragments of Nle-angiotensin (1-7) accelerate healing in dermal models," Journal of Peptide Research, 66 (Suppl):41-47.

Rodgers, et al. (2003) "Acceleration of healing, reduction of fibrotic scar, and normalization of tissue architecture by an angiotensin analogue, NorLeu3-A(1-7)," Plastic and Reconstructive Surgery, 111(3): 1195-1206.

Rodgers, et al., (2005) "Effect of NorLeu3-A(1-7) on scar formation over time after full-thickness incision injury in the rat," Wound Repair and Regeneration, 13(3): 309-317.

Rodgers, et al., (2002) "Accelerated recovery from irradiation injury by angiotensin peptides," Cancer Chemotherapy and Pharmacology, 49(5): 403-411.

Qu J. et al., (2003) "Reduced presence of tissue-repairing cells in wounds combined with the whole-body irradiation injury is associated with both suppression of proliferation and increased apoptosis"; Med Sci Monit; 9(10):BR370-7.

Jacob et al., (2010) "Ghrelin as a Novel Therapy for Radiation Combined Injury"; Mol Med 16(3-4) 137-143.

International Preliminary Report on Patentability for PCT/US2011/030142, mailed Oct. 2, 2012.

International Search Report for PCT/US2011/030142, mailed Jul. 13, 2011.

Mordwinkin, et al., "Toxicological and Toxicokinetic Analysis of Angiotensin (1-7) in Two Species," Journal of Pharmaceutical Sciences, 101(1): 373-380, Jan. 2012.

* cited by examiner

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 1

Asp Arg Xaa Tyr Ile His Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle

<400> SEQUENCE: 2

Asp Arg Xaa Tyr Ile His
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Nle
```

-continued

```
<400> SEQUENCE: 3

Asp Arg Xaa Tyr Ile
1               5
```

METHODS FOR TREATING COMBINED RADIATION AND THERMAL INJURY

RELATED APPLICATION

This application claims priority to U.S. Provisional Patent Application Ser. No. 61/317,897 filed Mar. 26, 2010, incorporated by reference herein in its entirety.

STATEMENT OF U.S. GOVERNMENT SUPPORT

This invention was made with U.S. government support under grant numbers 3RC1AI080976, and 3RC1AI080976S1 awarded by the National Institute of Allergy and Infectious Diseases. The U.S. Government has certain rights in the invention.

BACKGROUND OF THE INVENTION

It is known that radiation delays wound healing and this effect is seen in individuals who have been exposed to high levels of radiation, such as those present Hiroshima and Nagasaki at the time atomic bombs were detonated, and those present in and around Chernobyl after the nuclear meltdown at the Chernobyl nuclear facility. Individuals exposed to high levels of ionizing radiation will likely suffer not only from radiation sickness but also from thermal-induced injuries as a consequence of explosions and fires. Thus, therapeutics for use in treating combined radiation-thermal injury subjects are needed.

SUMMARY OF THE INVENTION

The present invention provides methods for treating a subject that has suffered combined (i) exposure to total body ionizing irradiation and (ii) burns, comprising administering to the subject an amount effective to treat the radiation effects and/or the burn of a peptide comprising at least 5 amino acids of a peptide of SEQ ID NO:1 (Asp-Arg-Nle-Tyr-Ile-His-Pro), or a pharmaceutical salt thereof. In one embodiment, the method results in improved survival in the subject compared to control. In another embodiment, the method results in accelerated burn healing compared to control. In a further embodiment, the subject has suffered second degree burns to one or more of the trunk, back, head, arm, or leg. In another embodiment, the subject has been exposed to total body ionizing irradiation of between 0.2 gray (G)y to 10 Gy; in further embodiments the subject has been exposed to total body ionizing irradiation of between 1 gray (G)y to 10 Gy or between 2 gray (G)y to 10 Gy. In another embodiment, the subject has suffered cumulative exposure to total body ionizing irradiation of at least 20 cGy. In a still further embodiment, the total body ionizing radiation is selected from the group consisting of beta-irradiation, gamma-irradiation, and X-ray. In another embodiment, the total body ionizing irradiation is caused by exposure to a radiation source selected from the group consisting of nuclear weapons, nuclear power facilities, computed tomography scan devices, X-ray devices, irradiators for bone marrow transplant conditioning, nuclear powered vehicles, and environment contaminated by radioactive materials. In another embodiment, the peptide is administered within three days of total body ionizing irradiation exposure. In further embodiments, the peptide comprises or consists of a peptide of SEQ ID NO:1 (Asp-Arg-Nle-Tyr-Ile-His-Pro), or a pharmaceutical salt thereof.

DETAILED DESCRIPTION OF THE INVENTION

Figure 1:
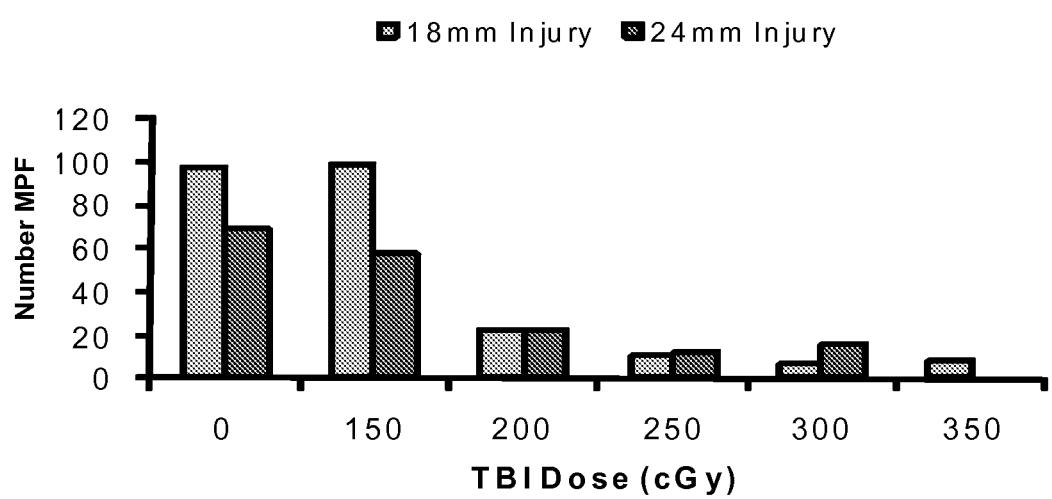
FIG. 1. Effect of TBI Dose and Burn Injury Size on Cyclin Positive Cells in the Injury area in a Guinea Pig Model.

The present invention provides methods for treating a subject that has suffered combined (i) exposure to total body ionizing irradiation and (ii) burns, comprising administering to the subject an amount effective to treat the radiation effects and/or the burn of a peptide comprising at least 5 amino acids of a peptide of SEQ ID NO:1 (Asp-Arg-Nle-Tyr-Ile-His-Pro), or a pharmaceutical salt thereof.

It is known that radiation delays wound healing and this effect is seen in individuals who have been exposed to high levels of radiation, and thus compounds that have been shown effective in wound healing may not be effective in healing of wounds or burns suffered in conjunction with exposure to total body ionizing radiation. The inventors have discovered that administration of Nle A(1-7) to subjects with combined total body ionizing radiation exposure and burns provides an unexpected benefit by increasing the burn healing response and increasing overall survival in such patients.

As is known in the art, "Nle A(1-7)" is a peptide having the amino acid sequence Asp-Arg-Nle-Tyr-Ile-His-Pro (SEQ ID NO:1). In various embodiments, the peptide comprises or consists of Asp-Arg-Nle-Tyr-Ile (Nle A(1-5)) (SEQ ID NO:3), Asp-Arg-Nle-Tyr-Ile-His (Nle A(1-6)) (SEQ ID NO:2), or Nle A(1-7).

The invention is appropriate for use with any type of ionizing radiation exposure accompanied by burns such as therapeutic or accidental X-ray, gamma ray, or beta particle exposure. Examples of ionizing radiation exposure suitable for treatment with the methods of the present invention include, but are not limited to, clinical radiation therapy, medical diagnostics using radioactive tracers, exposure to naturally occurring ionizing radiation sources such as uranium and radon, wartime exposure (ie: nuclear weapons), and accidental exposures including occupational exposure at nuclear power facilities, and medical and research institutions, computed tomography scan devices, X-ray devices, irradiators for bone marrow transplant conditioning, nuclear powered vehicles, and environment contaminated by radioactive materials.

The subject may be any suitable subject that can benefit from the methods of the invention. In one embodiment, the subject is a mammal, such as a human; pets such as dogs and cats; and livestock, including but not limited to cattle, sheep, goats, pigs, and chickens.

As used herein, "total body ionizing irradiation" means exposure to a source of ionizing irradiation that affects multiple organ systems.

In one embodiment, the subject has been exposed to total body ionizing irradiation of between 0.2 gray Gy to 12 Gy or greater; in further embodiments the subject has been exposed to total body ionizing irradiation of between 1 gray Gy to 12 Gy or greater; 2 gray y to 12 Gy or greater; 0.2 Gy to 10 Gy or greater; 1 Gy to 10 Gy or greater; 2 gray (G)y to 10 Gy or greater; 2.5 Gy to 10 Gy or greater; 3 Gy to 10 Gy or greater; 3.5 Gy to 10 Gy or greater; 4 Gy to 10 Gy or greater; 4.5 Gy to 10 Gy or greater; 5 Gy to 10 Gy or greater; 5.5 Gy to 10 Gy or greater; 6 Gy to 10 Gy or greater; 6.5 Gy to 10 Gy or greater; 7 Gy to 10 Gy or greater; 7.5 Gy to 10 Gy or greater; 8 Gy to 10 Gy or greater; 8.5 Gy to 10 Gy or greater; 9 Gy to 10 Gy or greater; greater than 10 Gy; or greater than 12 Gy. In another embodiment, the subject has suffered cumulative exposure to total body ionizing irradiation of at least 20 cGy. In various further embodiments, the subject has suffered cumulative exposure to total body ionizing irradiation of at least 25 cGy, 30 cGy, 35 cGy, 40 cGy, 45 cGy, 50 cGy, 55 cGy, 60 cGy, 65 cGy, 70 cGy, 75 cGy, 80 cGy, 85 cGy, 90 cGy, 95 cGy, 100 cGy, or greater.

The burn may be of any severity, preferably a partial thickness burn (i.e.: second-degree burn) to any body site, including but not limited to trunk, back, head, arm, or leg. The burn may be of any size, preferably at least 3 cm$^2$ in area, and more preferably at least 4, 5, 6, 7, 8, 9, or 10 cm$^2$ in area. In a further embodiment, the subject has suffered burns (such as second degree burns) over at least 10%, 20%, 30%, 40%, 50%, 60%, 79%, or more of their total body surface area.

In one preferred embodiment, the administering occurs within 0, 1, 2, or 3 days of radiation exposure. In other preferred embodiments, the peptide is administered in 1 ug per wound or higher; more preferably 10 ug or higher per wound. In various preferred embodiments, the peptide is administered in a dosage of 10 ug/cm$^2$, 50 ug/day, 100 ug/day, 200 ug/cm$^2$, 250 ug/day, 300 ug/cm$^2$, 350 ug/cm$^2$, 400 ug/cm$^2$, 450 ug/cm$^2$, 500 ug/day, or more.

As used herein, "treat" or "treating" means accomplishing one or more of the following: (a) reducing the severity of the burns or ionizing irradiation effects; (b) limiting or preventing development of symptoms characteristic of ionizing irradiation exposure; (c) inhibiting worsening of symptoms characteristic of ionizing irradiation exposure; (d) accelerated burn healing compared to control; and (e) improved survival. The biological effects of radiation depend on a number of factors such as the dose of radiation, duration of exposure, and the organ that is affected. Non-limiting examples of effects of exposure to total body ionizing irradiation include nausea, vomiting, diarrhea, impairment in central nervous system function (such as cognitive impairment, seizures, tremors, and ataxia), leukopenia, bone marrow destruction, intestinal destruction, infection (bacterial viral, fungal, etc.), shock, hypotension, hemorrhage, and death.

In various embodiments, the amount of peptide or pharmaceutical salt thereof is sufficient to provide the dosages discussed above. In exemplary embodiments, the amount of peptide or pharmaceutical salt thereof is sufficient to provide a dosage to a patient of between 0.01 µg/kg and 10 mg/kg; 0.1 µg/kg and 5 mg/kg; 0.1 µg/kg and 1000 µg/kg; 0.1 µg/kg and 900 µg/kg; 0.1 µg/kg and 900 µg/kg; 0.1 µg/kg and 800 µg/kg; 0.1 µg/kg and 700 µg/kg; 0.1 µg/kg and 600 µg/kg; 0.1 µg/kg and 500 µg/kg; or 0.1 µg/kg and 400 µg/kg.

Suitable acids which are capable of forming salts with the peptide include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with the peptide include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

The pharmaceutical compositions for use in the methods of the invention may be made up in a solid form (including granules, powders or suppositories) or in a liquid form (e.g., solutions, suspensions, or emulsions). The pharmaceutical compositions may be applied in a variety of solutions. Suitable solutions for use in accordance with the invention are sterile, dissolve sufficient amounts of the Nle A(1-7), and are not harmful for the proposed application. In this regard, the compounds of the present invention are very stable but are hydrolyzed by strong acids and bases. The compounds of the present invention are soluble in organic solvents and in aqueous solutions at pH 5-8. The pharmaceutical compositions may be subjected to conventional pharmaceutical operations such as sterilization and/or may contain conventional adjuvants. In one embodiment, the pharmaceutical composition is prepared for topical subcutaneous administration, the peptide or salt thereof may comprise from 0.0001% to 10% w/w; in one embodiment, not more than 5% w/w, and in a further embodiment from 0.01% to 2% w/w of the formulation.

In another embodiment, the peptide or salt thereof is prepared as a stable lyophilized peptide formulation that can be reconstituted with a suitable diluent to generate a reconstituted pharmaceutical compositions of the invention that are suitable for subcutaneous administration. When reconstituted with a diluent comprising a preservative (such as bacteriostatic water for injection), the reconstituted formulation may be used as a multi-use formulation. Such a formulation is useful, for example, where the subject requires frequent subcutaneous administrations of peptide. The advantage of a multi-use formulation is that it facilitates ease of use for the patient, reduces waste by allowing complete use of vial contents, and results in a significant cost savings for the manufacturer since several doses are packaged in a single vial (lower filling and shipping costs). Such reconstituted formulations would also be suitable for use with other types of parenteral administration.

The peptide or salts thereof can be administered by any suitable route, including but not limited to dermal, subcutaneous, intradermal, transdermal (for example, by slow-release polymers), intramuscular, intraperitoneal, intravenous, oral, aural, epidural, anal or vaginal (for example, by suppositories), and intranasal routes, infusion or bolus injection, or absorption through epithelial or mucocutaneous linings. In a preferred embodiment, the peptide or salts are administered transdermally and is formulated as a topical formulation, such as with hydroxyl ethyl cellulose (HEC). In one embodiment, the formulation is shielded to prevent degradation during stockpiling.

For administration, the pharmaceutical compositions are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, hydroxyethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. In a preferred embodiment, the peptide or pharmaceutical composition is administered topically. Any type of topical application means may be employed that permits the influx of the peptide or pharmaceutical composition into the thermally-injured tissue over a period of time. For example, an aqueous solution could be applied to the burn tissue through a gauze bandage or strip, or such a solution could be formulated so that a timed perfusion may be obtained (using liposomes, ointments, micelles, etc.) Methods for the production of these formulations with the peptides or pharmaceutical compositions of the present invention are apparent to those of ordinary skill in the art.

The peptide or salts thereof can further be derivatized to provide enhanced half-life, for example, by linking to polyethylene glycol. The peptide or salts thereof may comprise L-amino acids, D-amino acids (which are resistant to L-amino acid-specific proteases in vivo), a combination of D- and L-amino acids, and various "designer" amino acids (e.g., (β-methyl amino acids, Cα-methyl amino acids, and Nα-methyl amino acids, etc.) to convey special properties. Synthetic amino acids include norleucine for isoleucine.

In addition, the peptide or salts thereof can have peptidomimetic bonds. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such polypeptides are resistant to protease activity, and possess an extended half-live in vivo.

The peptide or salts thereof may be chemically synthesized or recombinantly expressed, each of which can be accomplished using standard methods in the art.

Nle A(1-7) or salts thereof may be administered as the sole treatment or in conjunction with other drugs or therapies useful in treating the condition in question, including but not limited to hydrogels, collagen sponges, and becaplermin gel.

Example 1

Guinea Pig Model for Combined Radiation/Body Injury (CRBI)

Figure 2:
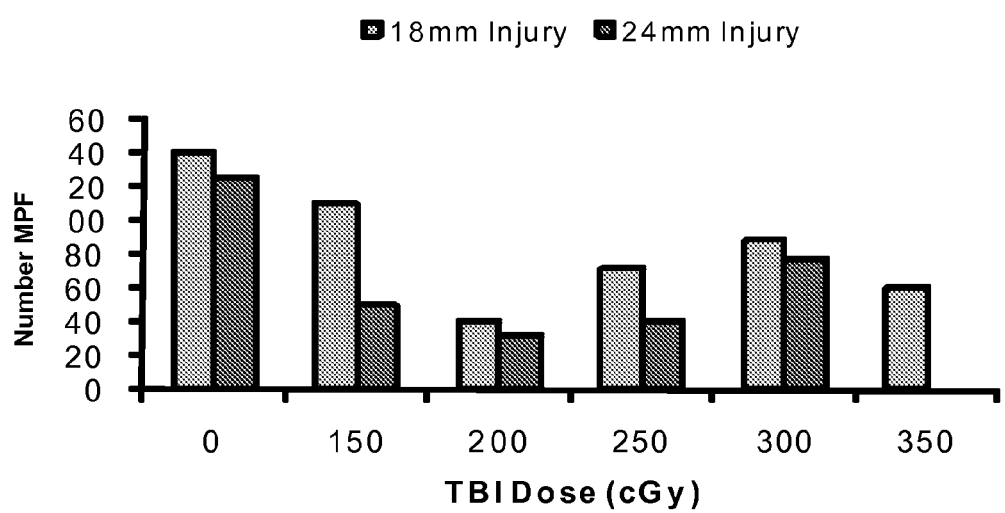
FIG. 2. Effect of TBI Dose and Burn Injury Size on Cyclin Positive Cells at the Edge of the Injury in a Guinea Pig Model FIG. 3. Effect of NorLeu$^3$-A(1-7) on Survival in a Guinea Pig Model of CRBI in guinea pigs following 200 cGy TBI.

A model for combined injury was developed in guinea pigs. The model development involved evaluation of five levels of total body irradiation (TBI) combined with 2 sizes of thermal injuries to determine the optimal combination to delay healing with minimal mortality. There was unacceptable mortality, particularly with the larger burn size at the two highest dose of TBI. The ability of TBI to delay healing was measured by the number of cyclin positive cells in the basal epidermis and hair follicle bulge. The proliferation data of day 14 animals are presented (FIGS. 1 and 2). At a TBI dose of 200 cGy and greater, there was a consistent reduction in the number of proliferating cells in the bulge region of the hair follicle and at the basal keratinocyte layer both at the burn site and at the edge of the burn. As these two cell populations are responsible for re-epithelialization of the thermal injury, 200 cGy combined with thermal injury both increased mortality and reduced healing.

Example 2

Efficacy of NorLeu$^3$-A(1-7) in CRBI Models

Figure 3:
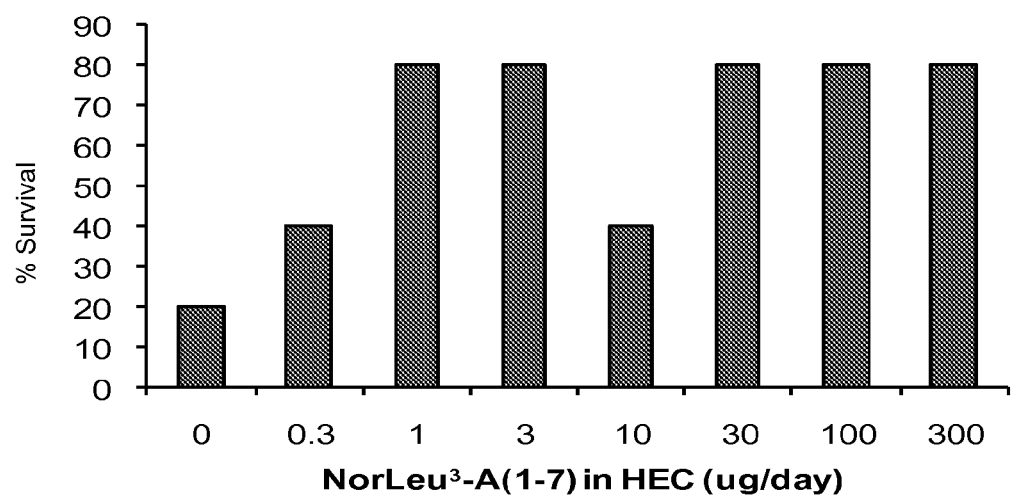
Figure 4:
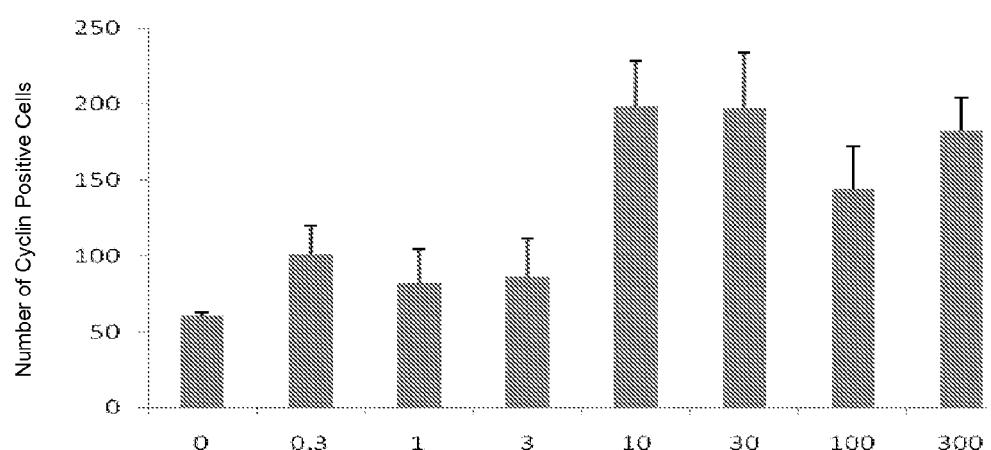
FIG. 4. NorLeu$^3$-A(1-7) increases proliferating cells in the basal keratinocyte layer at the edge of the burn.
Figure 5:
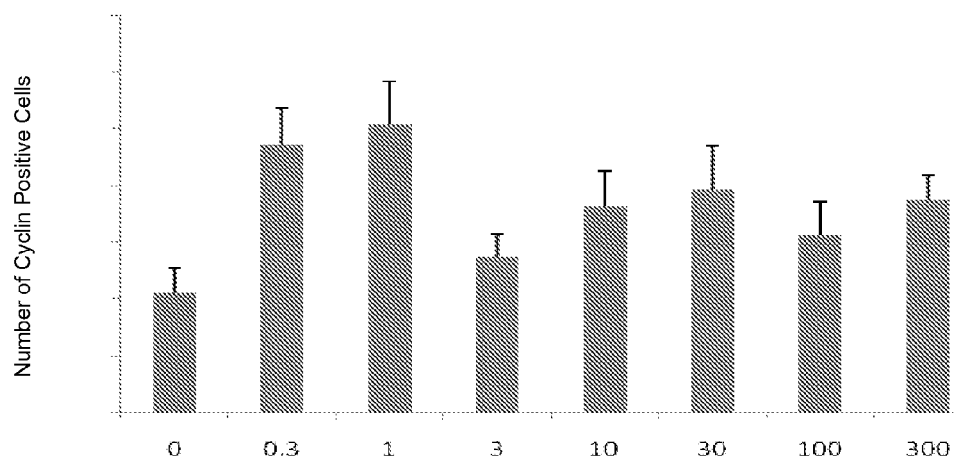
FIG. 5. NorLeu$^3$-A(1-7) increases proliferating cells in the hair follicle at the edge of the burn.
Figure 6:
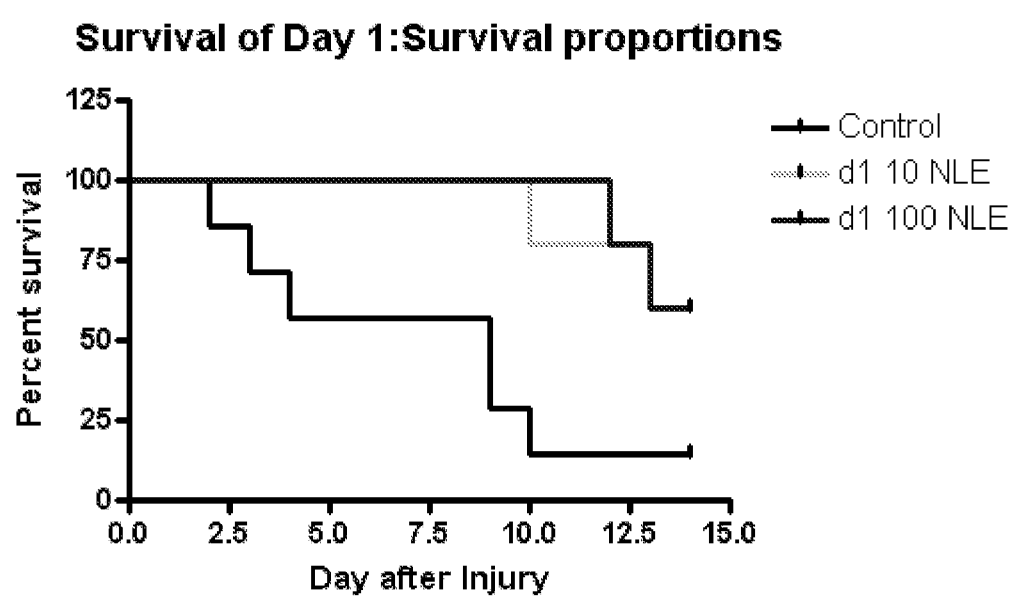
FIG. 6. Effect of NorLeu$^3$-A(1-7) on Survival in a Guinea Pig Model of CRBI in guinea pigs following 200 cGy TBI.

In a subsequent study, 200 cGy TBI was combined with 18 mm burn injuries in a NorLeu$^3$-A(1-7) dose-response study. On the day of thermal injury and daily through day 14, various concentrations of NorLeu$^3$-A(1-7) (0-300 μg/day) were applied to the site of thermal injury (FIG. 3). Application of 1 μg/wound/day NorLeu$^3$-A(1-7) and above reduced mortality associated with combined injury in guinea pigs. At doses of 10 μg/daily NorLeu$^3$-A(1-7) and above, there was an increase in the number of cells in the basal keratinocyte layer at the edge of the burn (FIG. 4). At all doses (except 3 μg/wound/day), NorLeu$^3$-A(1-7) increased the number of proliferating cells in the hair follicle bulge at the edge of the wound (FIG. 5).

Example 3

Determination of Time Point NorLeu$^3$-A(1-7) Can be Initiated in Guinea Pigs

A second study was conducted in this model to assess the length of time that treatment can be delayed and still reduce mortality. In this study, the guinea pigs underwent 200 cGy TBI and thermal injury 2 hours later. Treatment with placebo was started on day 0. Treatment with 10 or 100 μg/daily NorLeu$^3$-A(1-7) was initiated on day 0, 1, 2, 3 or 4. When treatment was started at days 0, 1, 2, or 3 survival was increased to approximately 40-60% versus 14% in the placebo-treated animals (FIG. 6-9). However, if the initiation of treatment was delayed until day 4, effectiveness was reduced.

Methods

For these studies, male Hartley guinea pigs weighing approximately 500 grams were purchased from Charles Rivers Laboratory (Charles Rivers, Mass.). The guinea pigs were housed in a 12:12 hour, light:dark, cycle in the USC Vivaria. The animals received 200 cGy TBI using a Cesuim 137 irradiator. One to two hours thereafter, the guinea pigs received a thermal injury. The thermal injuries were produced and post-operative care performed as described in Rodgers et al., 1997a,b, 2001. Briefly, after anesthesia, two burns were produced on each guinea pig with an 18 mm diameter solid brass rod, which was warmed in a 75° C. water bath. One end of the brass rod was placed on the back of the guinea pig for 50 seconds.

Each burn was treated with 2% HEC (vehicle for topical drug application) with and without NorLeu$^3$-A(1-7) in 0.05 mol/L phosphate buffer, pH 6.5, and was individually dressed. Treatment was started at various times after TBI and thermal injury as indicated below.

On day 14 after thermal injury, the guinea pigs was euthanized, the burned areas will be excised en bloc. The tissues were placed in 10% buffered formaldehyde solution overnight. Healing was measured by the number of proliferating cells at the injury site.

Immunohistochemical staining was performed with the avidin blotin-peroxidase conjugate method. After a final rinse in PBS the sections were incubated in 0.06% 3,3'-diaminobenzidine in PBS with 0.03% hydrogen peroxide for 5 minutes. After a counterstain was performed in modified Harris' hematoxylin-eosin, the sections were dehydrated and coverslipped with Permount.

With an Olympus Vanox-S AH-2 dissecting microscope and a magnification power of 100×, each section of the biopsy specimen was separated into either areas on the burn edge or the actual burn areas. The entire area of the burn and edge of the burn was embedded and examined histologically. In each section four to six consecutive medium-power fields (mpf, 100×) were evaluated. The cells that stained with the MIB-1 antibody were distinct brown color. All stained cells located within the hair follicles of the biopsy sections were counted. To count the MIB-1 stained cells each section on the slide was separated into individual medium power fields (mpf). Each field was then determined to be either a section on the edge of the burn or a part of the burn area itself. An edge was indicated by a positive stain showing brown epithelial cells along the edge of the section. A burn area was indicated by an absence of brown staining cells along the edge. The brown cells located within each hair follicle were counted one at a time under mpf magnification. To move to the next mpf a landmark was established, and the slide then moved to the next adjacent field.

Results

Figure 7:
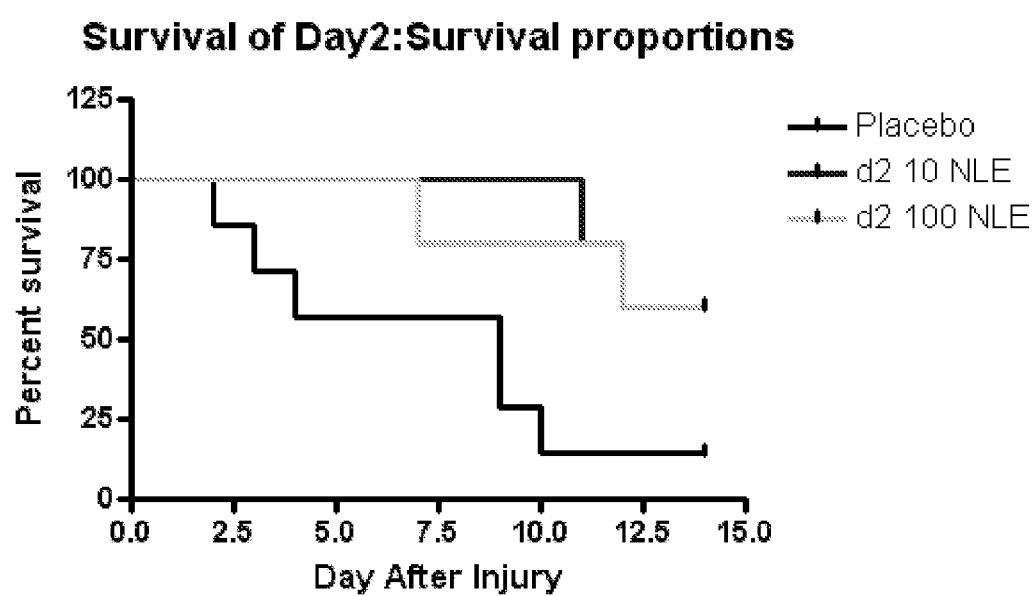
FIG. 7. Effect of NorLeu$^3$-A(1-7) on Survival in a Guinea Pig Model of CRBI in guinea pigs following 200 cGy TBI.
Figure 8:
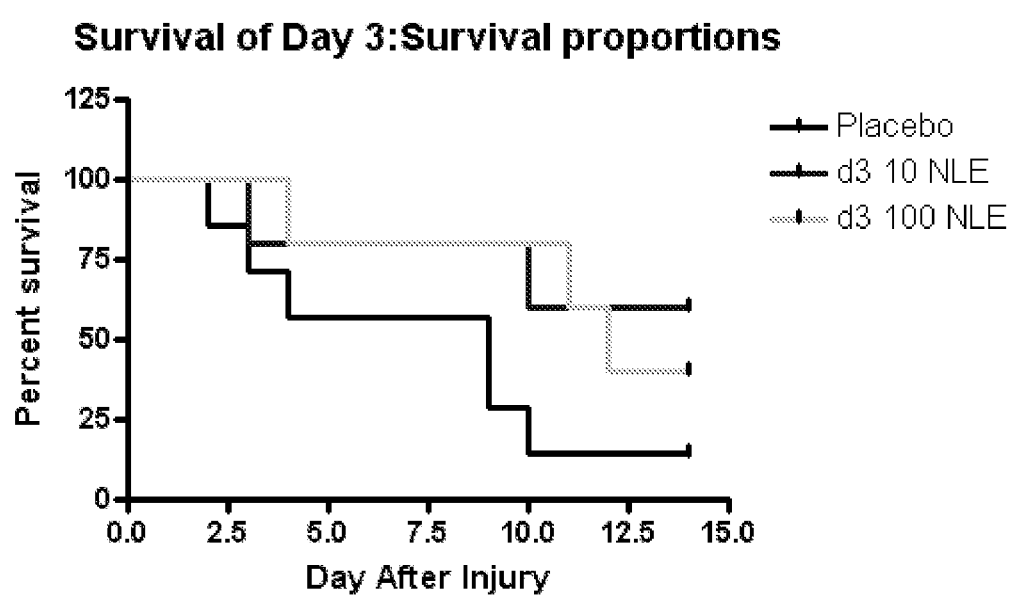
FIG. 8. Effect of NorLeu$^3$-A(1-7) on Survival in a Guinea Pig Model of CRBI in guinea pigs following 200 cGy TBI.
Figure 9:
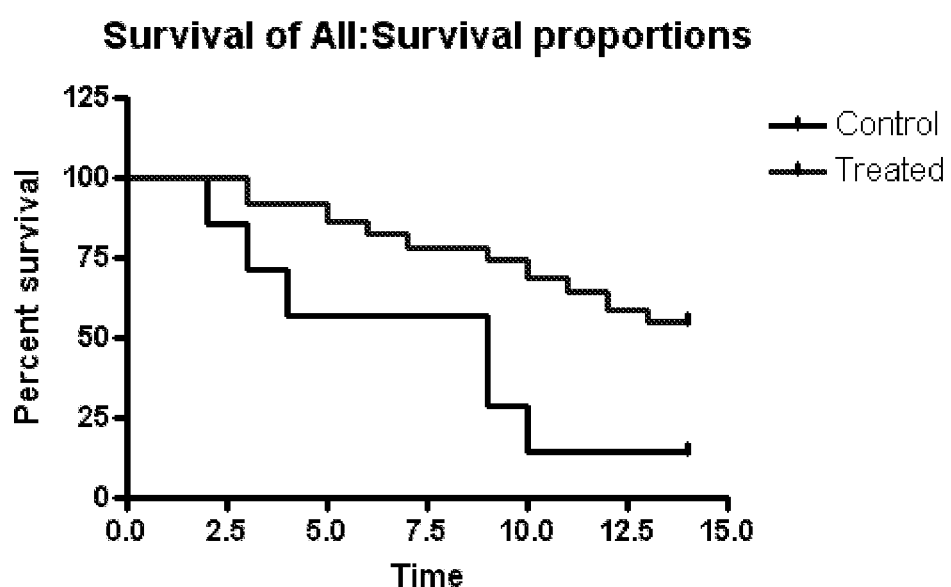
FIG. 9. Effect of NorLeu$^3$-A(1-7) on Survival in a Guinea Pig Model of CRBI in guinea pigs following 200 cGy TBI.

A second study was conducted in this model to assess the length of time that treatment can be delayed and still reduce mortality. In this study, the guinea pigs underwent 200 cGy TBI and thermal injury 2 hours later. Treatment with placebo was started on day 0. Treatment with 10 or 100 μg/day NorLeu$^3$-A(1-7) was initiated on day 0, 1, 2, 3 or 4. When treatment was started at days 0, 1, 2, or 3 after CRBI, survival was increased to approximately 40-60% versus 14% in the placebo-treated animals (FIG. 7). However, if the initiation of treatment was delayed until day 4, effectiveness was reduced.

Example 4

Figure 10:
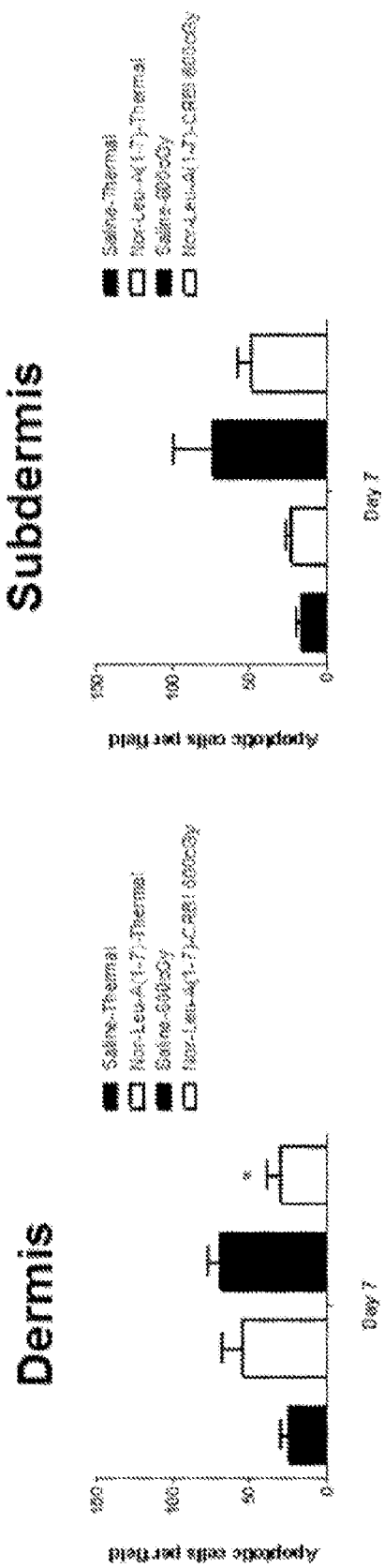
FIG. 10. NorLeu3-A(1-7) reduces apoptosis in the dermis and subdermis of thermal injuries in a mouse model of CRBI (10 sec scald at 70 C following 600 cGy TBI), but not at the site of thermal injury alone.

Mice received thermal injury only received a 7% total body surface area scald at 70 C for 10 seconds (under ketamine/xylazine anesthesia). Mice that received the combined injury received total body irradiation with a cesium irradiator at a dose of 6 Gy and 2 hours later received the same scald injury. For the data presented, the treatments were started immediately after the scald injury and the wound were bandaged with Tegaderm. Treatment was daily with 100 ul give per wound at a concentration of 1 mg/ml. The animals were euthanized on day 7. Apoptosis in the dermal tissue was measured by TUNEL assay. Data are shown in FIG. 10. NorLeu3-A(1-7) provides additional systems to mitigate delayed wound healing with the involvement of radiation.

---

We claim:

1. A method for improving survival in a subject that has suffered combined (i) exposure to total body ionizing irradiation of at least 0.2 Gy, and (ii) second degree burns over at least 7% of the subject's total body surface area, comprising administering to the subject an amount effective to treat the radiation effects and the burn of a peptide consisting of the peptide of SEQ ID NO:1 (Asp-Arg-Nle-Tyr-Ile-His-Pro), or a pharmaceutical salt thereof, wherein the method improves survival in the subject compared to control.

2. The method of claim 1, wherein the method results in accelerated burn healing compared to control.

3. The method of claim 1, wherein the subject has suffered second degree burns to one or more of the trunk, back, head, arm, or leg.

4. The method of claim 1, wherein the subject has been exposed to total body ionizing irradiation of between 0.2 Gy and 10 Gy.

5. The method of claim 1, wherein the subject has been exposed to total body ionizing irradiation of between 1 Gy and 10 Gy.

6. The method of claim 1, wherein the subject has been exposed to total body ionizing irradiation of between 2 Gy and 10 Gy.

7. The method of claim 1, wherein the subject has suffered cumulative exposure to total body ionizing irradiation of at least 20 cGy.

8. The method of claim 1, wherein the total body ionizing radiation is selected from the group consisting of beta-irradiation, gamma-irradiation, and X-ray.

9. The method of claim 1, wherein the total body ionizing irradiation is caused by exposure to a radiation source selected from the group consisting of nuclear weapons, nuclear power facilities, nuclear powered vehicles, and environment contaminated by radioactive materials.

10. The method of claim 1, wherein the peptide is administered within three days of total body ionizing irradiation exposure.

11. The method of claim 1, wherein the peptide is administered topically.

* * * * *